US005739910A

United States Patent [19]
Castor

[11] Patent Number: 5,739,910
[45] Date of Patent: Apr. 14, 1998

[54] METHOD FOR DETERMINING THE CONCENTRATION OF A SPECIFIC GAS AND AN ANALYZER

[75] Inventor: Rolf Castor, Hägersten, Sweden

[73] Assignee: Siemens Elema AB, Solna, Sweden

[21] Appl. No.: 756,690

[22] Filed: Nov. 26, 1996

[30] Foreign Application Priority Data

Dec. 11, 1995 [SE] Sweden .................. 9504417

[51] Int. Cl.[6] .................. G01J 4/00
[52] U.S. Cl. .................. 356/369; 356/437
[58] Field of Search .................. 356/364, 369, 356/381, 382, 432, 436, 437, 128; 250/225

[56] References Cited

U.S. PATENT DOCUMENTS

| | | | |
|---|---|---|---|
| 4,906,844 | 3/1990 | Hall | 356/369 |
| 5,107,105 | 4/1992 | Isobe | 356/369 |
| 5,420,680 | 5/1995 | Isobe et al. | 356/369 |
| 5,563,707 | 10/1996 | Prass et al. | 356/128 |

FOREIGN PATENT DOCUMENTS 0 256 314   2/1988   European Pat. Off. .
2 290 245  12/1995   United Kingdom .

Primary Examiner—Hoa Q. Pham
Attorney, Agent, or Firm—Hill, Steadman & Simpson

[57] ABSTRACT

A method and an analyzer for determining the concentration of and/or identifying a specific gas are described. The analyzer has a test chamber through which a gas sample is carried. The gas sample then passes across a first substrate on which a first coating and a second coating are arranged. The second coating is made of a substance which selectively absorbs a specific gas, or a specific group of gases. A light source directs a light beam with a pre-defined polarization at the substrate and coatings. Polarization of the ensuring reflected light beam changes due to reflection in and interaction with the coatings. This change is determined by a calculation unit by determining the reflected light beam's polarization in a photodetector. Adsorption causes polarization changes which are only related to the concentration of the specific gas which can accordingly be identified.

13 Claims, 1 Drawing Sheet

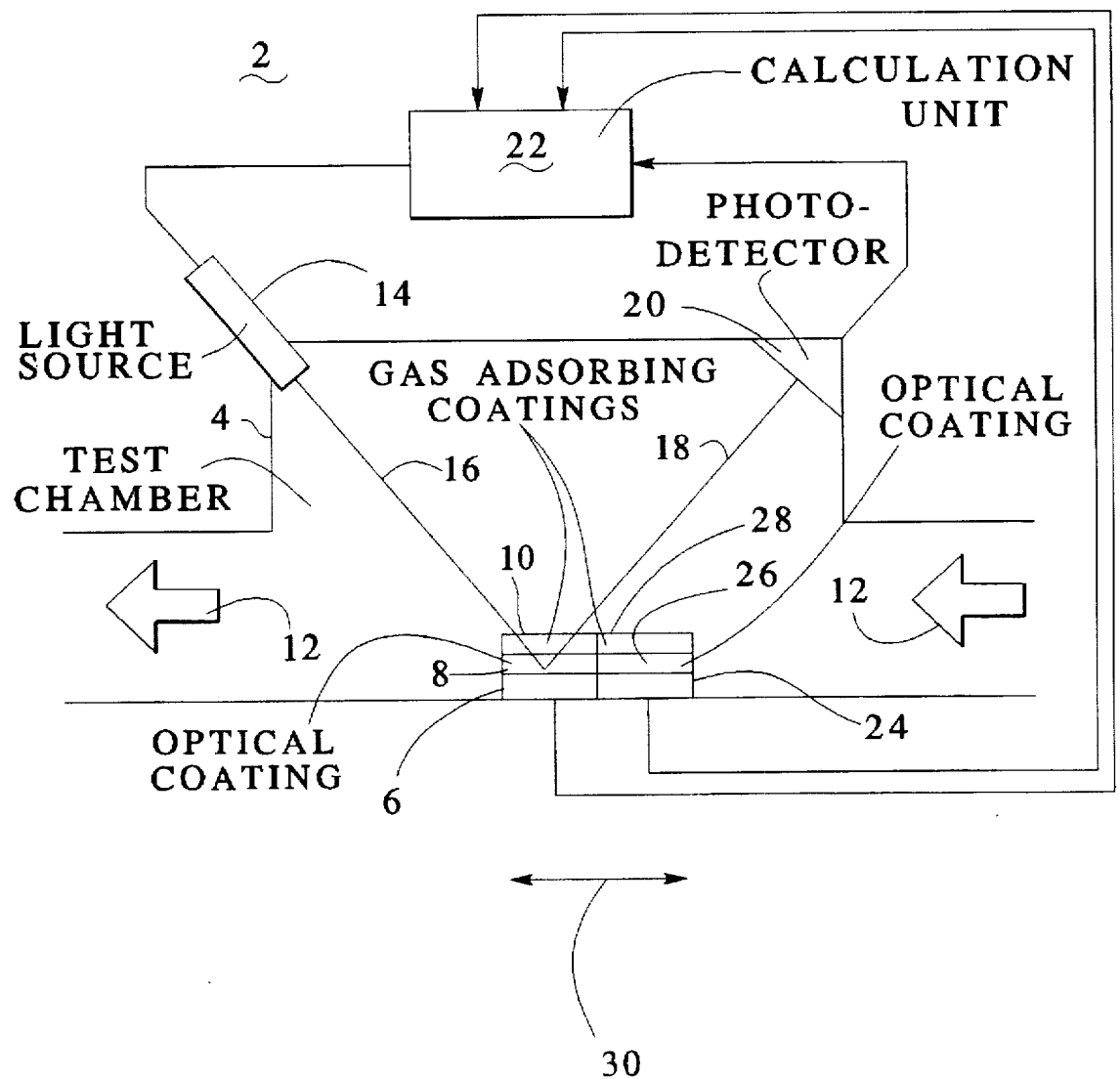

METHOD FOR DETERMINING THE CONCENTRATION OF A SPECIFIC GAS AND AN ANALYZER

BACKGROUND OF THE INVENTION

1. Field of the Invention

The present invention is directed to a method for determining the concentration of a specific gas in a gas mixture, as well as to an analyzer for identifying and/or determining the concentration of a specific gas in a gas mixture.

More specifically the present invention is directed to the use of an ellipsometer for determination of the concentration of a specific gas in a gas mixture, preferably an anesthetic gas in a breathing gas, of the type wherein the ellipsometer emits light onto a measurement surface and wherein light reflected from the measurement surface is directed and analyzed to identify differences in the polarization of incident light and reflected light.

2. Description of the Prior Art

Achieving faster, better and/or more reliable methods and analyzers for identifying a specific gas in a gas mixture and, in particular, determining the concentration of a specific gas in a gas mixture are of interest in many technical fields.

One of these fields concerns determination of the concentration of an anesthetic agent in a gas mixture supplied to a patient during anesthesia. Two common analysis methods in the anesthesia art are IR spectrophotometry and crystal frequency analysis. The latter is based on changes in the frequency of an oscillating quartz crystal caused by the adsorption of anesthetic gas molecules by an adsorption coating applied to the quartz crystal.

Both methods display excellent properties, provided the anesthetic gas used is known. The most common anesthetic gases are desflurane, enflurance, halothane, isoflurane and servoflurane. These anesthetic gases have very similar physical properties. The small differences between them are virtually invisible when the gases are used, since they are normally supplied at different concentrations. Thus measurement using either method yields about the same signal strength for the measurement signal. If the wrong anesthetic gas is inadvertently used, an erroneous concentration might be supplied.

Ellipsometry is a well-known analysis method for examining extremely thin films, i.e. for measuring the thickness of extremely thin films. The method is based on an analysis of the way in which the thin film affects the polarization of a light beam. A number of ellipsometry methods are known, e.g. null ellipsometry, photometric ellipsometry and PCSA ellipsometry. They do not require detailed description herein, since they are exhaustively described elsewhere.

SUMMARY OF THE INVENTION

An object of the present invention is to provide an improved method for determining the concentration of a specific gas in a gas mixture.

Another object of the present invention is to provide an analyzer for performing the method and corresponding analyses.

Another object of the invention is to provide a new use for ellipsometry.

The above object of providing an improved method is achieved in accordance with the principles of the present invention for a method for determining the concentration of a specific gas in a gas mixture wherein at least a part of the gas mixture is passed across the first coating which is applied to a light-reflective surface, the first coating being made of a first substance which absorbs the specific gas, wherein a light beam, with a pre-defined polarization, is directed at the first coating, wherein the polarization of the light beam reflected from the coating and the light-reflecting surface is detected, wherein a change in the polarization of the reflected light beam as compared to the incident light beam is detected, this change being caused by adsorption of the specific gas in the first substance which affects the complex refractive index of the first coating, and wherein the concentration of the specific gas is determined from the change in polarization.

The method bears a certain resemblance to ellipsometry. Light with a specific polarization is emitted at the measurement area where it passes through one coating and is reflected off a reflective area. Part of the light is reflected off the coatings's surface and part of the light is reflected, one or several times, between the surface of the coating and the reflective surface. This combination causes the plane of light polarization to be changed. The magnitude of the change depends on the coating's complex refractive index. A major difference of the inventive method from conventional ellipsometry, however, is the use of a layer or a coating of a substance which absorbs a specific gas. When the specific gas is adsorbed by the coating, the complex refractive index changes. This change depends on the concentration of the specific gas. The concentration of the specific gas can be determined by analyzing the way these changes affect the polarization of the light. Calibration can be performed against known concentrations of the specific gas.

It is an advantage if the coating is made of a substance which selectively adsorbs only the specific gas or only gases with similar molecular structures. The method's use naturally governs the type of substance needed for the coating. If, for example, the c concentration of other gases in the gas mixture remains constant, a reference value can be established when the specific gas is absent. The coating then does not need to be as selective.

The method can be combined with a known method, such as the aforementioned crystal frequency analysis, in order to ensure completely reliable identification of the specific gas. The reflective surface should then approximately be part of an oscillating crystal. The gas can then be analyzed with both methods, and ensuing measurement values can be mathematically combined in different ways to yield a unique signal for each specific gas. The measurements can be performed alternating (one measurement at a time) or simultaneously. The advantage of simultaneous measurement is that measurement is reliably made on the exact same sample.

This was not previously possible when combined concentration measurements, using a number of measurement methods on a gas mixture, were used.

The method can also be combined with other measurement methods, such as IR spectrophotometry. Here, the analysis can be made on essentially the same sample by selecting radiation paths appropriately.

Alternatively, two different substances, which adsorb the specific gas in different ways, can be placed next to each other. Measurements are then performed on both coatings, either in parallel or sequence. Mathematical combining of the two measurements can supply a better value for concentration and better prospects for identification. Another option is to use two parallel coatings made of the same substance but with different thicknesses.

The above object of providing an analyzer is achieved in accordance with the principles of the present invention in an analyzer for identifying and/or determining the concentration of a specific gas in a gas mixture having a measurement unit through which at least a part of the gas mixture to be analyzed is passed, a reflective surface arranged in the measurement unit, a first coating arranged on the reflective surface, the first coating being made of a substance which adsorbs the specific gas, a light source which emits a light beam with a predetermined polarization at the reflective surface, a photodetector for measuring a light beam reflected from the reflective surface, the reflective light beam having interacted with the first coating, and a calculation unit which determines the concentration of the specific gas from differences between the incident light beam striking the reflective surface and the light reflected therefrom.

In one embodiment, the photodetector can be of a type for detecting the polarization of the reflective light beam, and the calculation unit determines the concentration of the specific gas from the difference in polarization between the incident light beam and the reflected light beam. Alternatively, the photodetector can be of a type which detects the intensity of the reflected light beam in a specific polarization direction, and the calculation unit, using the intensity in the absence of the specific gas, calculating the concentration of the specific gas from the extent that the intensity of the reflected light beam departs from the reference intensity.

The analyzer is able to perform the above-described method according to the invention as well as other types of measurements. Thus, the analyzer can also measure intensity changes on a pre-defined polarization plane, and concentration can then be determined from the change in intensity when measured intensity is compared to a reference value when the concentration of the specific gas is zero.

DESCRIPTION OF THE DRAWINGS

The FIGURE shows an embodiment of an analyzer for identifying and/or determining the concentration of a specific gas in a gas mixture, constructed and operating in accordance with the principles of the present invention.

DESCRIPTION OF THE PREFERRED EMBODIMENTS

The analyzer shown in the drawing includes a test chamber 4 in which a first substrate 6 is arranged. A first coating 8 is applied to the first substrate 6. The first coating 8 has pre-defined optical properties and is inert to ambient air. A second coating 10 is arranged on the first coating 8. The second coating 10 is made of a substance which adsorbs a specific gas, a specific group of gases or a number of specific groups of gases. Selection of the proper substance is made based on the specific gas to be analyzed and the constitution of gases accompanying the specific gas in a test gas. Adsorption is governed by the ambient concentration of the absorbed gas. The optical properties of the second coating 10, its complex refractive index in particular, change in relation to the amount adsorbed.

The test gas is sent through the test chamber 4, and indicated by the arrows 12. The test gas can be a sample from a larger quantity of a mixture of gases to be analyzed or can consist of the entire mixture of gases to be analyzed. When anaesthetic gases are analyzed, the test gas is a breathing gas. The test gas can flow continuously or discontinuously through the test chamber 4.

The analysis of the test gas is carried out as follows. A light beam 16 with a predefined polarization is emitted by a light source 14. The light source 16 is partially reflected off the second coating 10 and is partially transmitted through the second coating 10 to the first coating 8. The light beam 16 is partially reflected off the first coating 8 and is partially transmitted through the first coating 8 to the substrate 6. Most of the light beam 16 is reflected off the substrate 6. Multiple reflections also occur between the coatings 8 and 10.

In total, a composite, reflected light beam 18 results. The reflected light beam 18 is detected with a photodetector 20 and analyzed in a calculation unit 22.

Normal ellipsometry calculations can be used on the reflected light beam 18, whereupon the photodetector 20 determines the polarization of the reflected light beam 18. In this case, however, the calculation unit 22 then determines the concentration of the specific gas based on the differences in the polarization of the incident light beam 16 and the reflected light beam 18.

A number of options for a method for analyzing gases then are possible. First, it is assumed that the second coating 10 adsorbs a wide range of gases.

When a known gas, having a known composition, flows through the test chamber 4, it will be adsorbed by the second coating 10, causing a change in polarization. Polarization does not change thereafter as long as there is no change in the partial pressure of each gas component. A new gas component can then be introduced. The new gas component is adsorbed, and polarization changes. When the calculation unit 22 is calibrated against a known concentration of the new gas component, the concentration of the new gas component can be continuously determined based on polarization changes.

One practical application for this procedure is in the analysis of anesthetic gases. A breathing gas with a known composition is sent to the test chamber 4, and equilibrium in adsorption then occurs. Calibration is performed against a known concentration of a specific anesthetic gas. The concentration of the anesthetic gas can then be (continuously) monitored. Any systematic changes in pressure of the gas mixture (due to inspirations and expirations) can be compensated. Compensation can be based on the cyclic character of the changes and/or based on information from a ventilator. Calibration can also be made based on a cyclic variation of pressure and/or composition.

The procedure is much simplified if the second coating 10 only adsorbs one or a few specific gases. A simple calibration is then sufficient.

The substrate 6, or the first coating 8, can be an oscillating crystal to ensure identification of a specific gas component (or to confirm that the right gas component is being used). As noted above, determination of concentration by means of crystal frequency analysis is known. The oscillation frequency of the crystal is thus affected by the adsorption and a concentration signal is generated. Mathematical combining of the two measurement methods yields unique signal combinations which can be compared to the reference value obtained for each specific gas, e.g. for different relevant anesthetic gases. This makes identification possible.

The measurements can be made alternating or simultaneously. When measurements are made simultaneously, calculation of the change in polarization will probably need to be compensated for the crystal's oscillations. Measurements are clearly made on one and the same sample. This improves reliability, compared to known methods in which test samples are transferred from test chamber to test chamber.

Alternatively, measurements can be performed on some other substance which adsorbs gases in some other way. In the FIGURE, this is illustrated with a second substrate 24 on which a third coating 26 and a fourth coating 28 are arranged. The first substrate 6, with the first and second coatings 8 and 10, and the second substrate 24, with the third and fourth coatings 26 and 28, can be alternately moved into the light beam 16, as the arrow 30 shows. This is a cheaper procedure than utilization of a second light source and photodetector array.

A combination of alternatives is also possible in which both the substrates 6 and 24, or the first and third coatings 8 and 26, are oscillating crystals. Measurements can then be made simultaneously on alternating substrates, i.e. ellipsometry can be performed on the first substrate 6 and crystal frequency analysis can be performed on the second substrate 24.

Instead of using ellipsometry as described above, the analyzer's photodetector can be devised to measure variations in the intensity of one or a number of specific polarization directions in the determination of the concentration of the specific gas.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for determining a concentration of a specific gas in a gas mixture, comprising the steps of:

passing at least a portion of said gas mixture across a first coating applied to a light-reflective surface, said first coating adsorbing said specific gas;

directing an incident light beam having a predetermined polarization onto said first coating and said light-reflective surface;

detecting polarization of a reflected light beam formed by said incident light beam reflected off of said coating and said light-reflective surface;

determining changes in polarization between said incident light beam and said reflected light beam caused by adsorption of said specific gas by said first coating which affect a complex refractive index of said first coating; and determining the concentration of said specific gas from said changes in polarization.

2. A method as claimed in claim 1, comprising the additional step of:

disposing at least one additional coating between said first coating and the reflective surface.

3. A method as claimed in claim 2 wherein the step of disposing at least one additional coating between said first coating and said reflective surface comprising disposing at least one additional coating next to said first coating which also affects changes in polarization of said incident light beam, and comprising the additional steps of determining changes in the polarization of said incident light beam and said reflective light beam caused by adsorption of said specific gas in said additional coating, and determining the concentration of said specific gas from the changes in polarization caused by each of said first coating and said additional coating.

4. A method as claimed in claim 1, comprising the additional steps of:

oscillating said light-reflected surface while said incident light beam is directed at said light-reflective surface and said first coating, at an oscillating frequency which varies with an amount of said specific gas adsorbed in said first coating;

making an additional determination of the concentration of said specific gas from changes in said oscillation frequency; and identifying said specific gas by mathematically combining the concentration determined by said changes in polarization and the concentration determined from said changes in the oscillation frequency.

5. An analyzer for determining a concentration of a specific gas in a gas mixture, comprising:

a measurement unit through which at least a portion of said gas mixture is passed;

a reflective surface disposed in said measurement unit;

a first coating on said reflective surface, said first coating adsorbing said specific gas;

a light source disposed to emit an incident light beam with a predetermined polarization onto said reflective surface;

a photodetector which measures a reflected light beam, said reflected light beam being produced by said incident light beam interacting with said first coating and said reflective surface; and calculation means for determining the concentration of said specific gas from a difference between said incident light beam and said reflected light beam.

6. An analyzer as claimed in claim 5 wherein said photodetector comprises means for detecting polarization of said reflected light beam, and wherein said calculation means comprises means for determining the concentration of said specific gas from a difference between the polarization of the incident light beam and the polarization of said reflected light beam.

7. An analyzer as claimed in claim 5 wherein said photodetector comprises means for detecting an intensity of said reflected light beam in a specified polarization direction, and wherein said calculation means comprises means for determining the concentration of the specific gas from a deviation of said intensity from an intensity of a reflected light beam in the absence of said specific gas.

8. An analyzer as claimed in claim 5 further comprising an oscillating crystal on which said reflective surface is mounted, said oscillating crystal having an oscillation frequency which varies dependent on an amount of said specific gas adsorbed by said first coating, and wherein said calculation means comprises means for determining the concentration of said specific gas from changes in the oscillation frequency of said oscillating crystal.

9. An analyzer as claimed in claim 8 wherein said calculation unit comprises means for identifying the specific gas from two separate concentration determinations.

10. An analyzer as claimed in claim 5 further comprising at least one additional coating disposed on said reflective surface.

11. An analyzer as claimed in claim 10 wherein said at least one additional coating is disposed next to said first coating and comprises material which changes in polarization dependent on adsorption of said specific gas, and wherein said calculation unit comprises means for identifying said specific gas from the polarization change caused by said first coating and the polarization change caused by said additional coating.

12. A method for continuously determining a concentration of a specific gas in a gas mixture comprising the steps of:

passing said gas mixture through an ellipsometer;

directing light at a coating on a reflective surface in said ellipsometer;

detecting light reflected from said reflective surface and analyzing differences in polarization of incident and reflected light; and coating said reflective surface with a substance which adsorbs said specific gas and continuously flowing said gas mixture over said substance.

13. A method as claimed in claim 12 comprising the additional step of vibrating said reflective surface with an oscillation frequency which changes dependent on adsorption of said specific gas in said substance, determining changes in the oscillation frequency as a complementary measure of said concentration of said specific gas, and producing a final measurement of the concentration of said specific gas from the differences in the polarization and the changes in oscillation frequency.

* * * * *